(12) United States Patent
Nishizawa et al.

(10) Patent No.: US 7,544,438 B2
(45) Date of Patent: Jun. 9, 2009

(54) ELECTRON MEDIATOR, ELECTRON MEDIATOR IMMOBILIZED ELECTRODE, AND BIOFUEL CELL USING THE ELECTRODE

(75) Inventors: Matsuhiko Nishizawa, Sendai (JP); Tomokazu Matsue, Sendai (JP); Jun-ichi Kosuge, Tokai-mura (JP); Noboru Fukasaku, Tokai-mura (JP)

(73) Assignee: Daiichi Pure Chemicals Co., Ltd, Tokyo (JP)

( * ) Notice: Subject to any disclaimer, the term of this patent is extended or adjusted under 35 U.S.C. 154(b) by 303 days.

(21) Appl. No.: 10/807,489

(22) Filed: Mar. 23, 2004

(65) Prior Publication Data

US 2005/0049313 A1    Mar. 3, 2005

(30) Foreign Application Priority Data

Sep. 2, 2003   (JP)   ............... 2003-309946

(51) Int. Cl.
*H01M 2/14* (2006.01)
*H01M 4/86* (2006.01)
*C12Q 1/00* (2006.01)
*C12N 11/08* (2006.01)

(52) U.S. Cl. ............... 429/43; 204/242; 204/403.1; 204/403.14; 205/777.1; 429/12; 429/42; 435/174; 435/175; 435/180; 435/181; 435/817

(58) Field of Classification Search ............... None
See application file for complete search history.

(56) References Cited

U.S. PATENT DOCUMENTS

| | | | | |
|---|---|---|---|---|
| 5,264,104 A | * | 11/1993 | Gregg et al. | 204/403.09 |
| 5,443,701 A | * | 8/1995 | Willner et al. | 205/777.5 |
| 5,972,199 A | * | 10/1999 | Heller et al. | 205/777.5 |
| 6,461,496 B1 | * | 10/2002 | Feldman et al. | 205/777.5 |
| 6,531,239 B2 | * | 3/2003 | Heller | 429/43 |
| 2003/0087144 A1 | * | 5/2003 | Sun et al. | 429/43 |

FOREIGN PATENT DOCUMENTS

| JP | 10-310799 | | 5/2000 |
|---|---|---|---|
| JP | 2000133297 | * | 5/2000 |

OTHER PUBLICATIONS

Cheng, et al,; "Development of dimethyl sulfoxide biosensor using a mediator immobilized enzyme electrode"; (2003); *The Analyst;* full paper.
Wang, et al.; "Oxygen-independent poly(dimethylsiloxane)-based carbon-paste glucose biosensors"; (2002); *Biosensors and Bioelectronics;* 17: 999-1003.
Miki, et al.; "Bioelectrocatalysis at NAD-Dependent Dehydrogenase and Diaphorase-Modified Carbon Paste Electrodes Containing Mediators"; (1989); *Analytical Sciences;* vol. 5, pp. 269-274.
Katrlik, et al.; "Composite alcohol biosensors based on solid binding matrix"; (1998); *Biosensors & Bioelectronics;* vol. 13, No. 2, pp. 181-191.

* cited by examiner

*Primary Examiner*—Herbert J. Lilling
(74) *Attorney, Agent, or Firm*—Sonnenschein Nath & Rosenthal LLP

(57) ABSTRACT

An object of the present invention is to provide a highly functional mediator capable of smoothly proceeding electron transfer between an electrode and a biocatalyst based on the premise that the mediator excels in safety and cost and to provide an electrode and a cell with sufficient amount of such a mediator molecule immobilized efficiently and strongly. The present invention provides a mediator mediating electron transfer between an enzyme and an electrode and containing a quinone molecule derivative, in particular, a mediator containing a $VK_3$ derivative. In addition, the present invention provides an electrode and a biofuel cell to which those mediators are applied.

28 Claims, 8 Drawing Sheets

ELECTRON MEDIATOR, ELECTRON MEDIATOR IMMOBILIZED ELECTRODE, AND BIOFUEL CELL USING THE ELECTRODE

RELATED APPLICATIONS

This application claims priority to Japanese Patent Application No. 309946/2003 filed Sep. 2, 2003.

BACKGROUND OF THE INVENTION

1. Field of the Invention

The present invention relates to an electron mediator (hereinafter, simply referred to as "mediator") used in a biofuel cell or a biosensor employing a bioenzyme as a catalyst, an electron mediator immobilized electrode, and a biofuel cell using the electrode.

2. Description of the Related Art

A bioelectrochemical fuel cell (hereinafter, referred to as "biofuel cell") is drawing increasing attention from considerations in safety and cost of fuel cell materials. The biofuel cell employs a biocatalyst such as a microorganism or an enzyme and uses biomass for an anode fuel. Examples of the biomass include hydrogen, methanol, and in addition, glucose, which is very easily handled and which abundantly exists as a source of nutrition for the human beings. The biofuel cell employs a biocatalyst, and hence has a characteristic of allowing operation under mild conditions of a physiological environment such as room temperature, neutrality, and atmospheric pressure. Theoretical electromotive force of a glucose/$O_2$-type biofuel cell of 1.25 V is provided from a difference between a redox potential of the glucose, which is an anode fuel, and a redox potential of the $O_2$, which is a cathode fuel. A redox reaction of glucose using an electrode is very slow in actuality, requiring an enzyme to be used as an electrocatalyst. However, a redox reaction active center of an enzyme is covered with a polymer protein. Thus, electrolytic oxidation of the glucose would not be possible without using a mediator carrying out electron transfer between an enzyme and an electrode.

Possibility for miniaturization of such a biofuel cell is expected, and the biofuel cell may be applied in the field of medicine for an implanted biological device which can operate on its own such as a nanorobot, a micropump, a pace maker, or a miniature glucose sensor.

Examples of a mediator for such a biological device usually included a mediator employing an osmium complex for a biofuel cell and a mediator employing an iron cyanide complex for a glucose sensor. However, those mediators had problems in safety and cost.

Further, JP 2000-133297 A discloses a mediator for a biofuel cell composed of a compound having a thionine skeleton and a 2-hydroxy-1,4-naphthoquinone skeleton. The mediator has the compound immobilized on an electrode for reducing an amount of the mediator used so that diffusion of the mediator in an electrode solution does not become rate controlling.

Immobilization of the mediator on an electrode involves subjecting the electrode to plasma treatment and further subjecting the electrode to treatment with 3-aminopropyltriethoxysilane, to thereby form an electrode with an amino group introduced to an electrode surface. The immobilization further involves: immobilizing long-chain alcohol on a carbon electrode surface through dehydration condensation; and immobilizing the immobilized long-chain alcohol and 2-hydroxy-1,4-naphthoquinone through dehydration condensation.

Such immobilization involves complicated operations, and has had practical problems. The immobilization involved monomolecular layer modification, and hence an amount of the mediator immobilized became small and thus an amount of an enzyme immobilized was also restricted, resulting in limited reactivity.

Further, a non-patent document (K. Miki, T. Ikeda, S. Todoroki, and M. Senda, Analytical Sciences, 1989, 5(3), 269) discloses 2-methyl-1,4-naphthoquinone ($VK_3$) as a mediator. The mediator and $NAD^+$ are mixed with a carbon paste constituting an electrode, and diaphorase and dehydrogenase are injected to an electrode surface. Then, the electrode surface is covered with a nylon film to be used as a biocatalyst electrode.

The biocatalyst electrode has the mediator merely sealed in the paste physically. Therefore, the biocatalyst electrode has had practical problems in that a mediator molecule elutes from the electrode surface in long-term use to degrade performance as an electrode.

SUMMARY OF THE INVENTION

The present invention has been made in view of solving the above problems of conventional techniques, and an object of the present invention is therefore to provide a following mediator, electrode, and biofuel cell. In other words, an object of the present invention is to provide a highly functional mediator which smoothly proceeds electron transfer between an electrode and a biocatalyst based on the premise that the mediator excels in safety and cost. Further, another object of the present invention is to provide an electrode and a cell with a sufficient amount of such a mediator molecule immobilized efficiently and strongly.

(1) A mediator which mediates electron transfer between an enzyme and an electrode, characterized by including a quinone molecule derivative.

(2) A mediator according to item (1), in which the quinone molecule derivative is a naphthoquinone molecule derivative.

(3) A mediator according to item (2), in which the naphthoquinone molecule derivative is one or more kinds of a naphthoquinone molecule chosen from the group consisting of a sodium anthraquinone-2-sulfonate (AQS) derivative and a 2-methyl-1,4-naphthoquionone ($VK_3$) derivative.

(4) A mediator according to item (2), in which the naphthoquinone molecule derivative is a 2-methyl-1,4-naphthoquinone ($VK_3$) derivative.

(5) A mediator according to item (4), in which the 2-methyl-1,4-naphthoquinone ($VK_3$) derivative is 2-methyl-1,4-naphthoquinone ($VK_3$) modified with one or more kinds of a functional group selected from the group consisting of an amino group, a carboxyl group, a chloroformyl group, a succinimide oxycarbonyl group, an alkyl metal sulfosuccinimide oxycarbonyl group, a pentafluorophenyl oxycarbonyl group, a p-nitrophenyl oxycarbonyl group, a hydroxyl group, a formyl group, a halogen group, a maleimide group, an isothiocyanate group, and an oxiranyl group.

(6) A mediator according to item (5), in which the 2-methyl-1,4-naphthoquinone ($VK_3$) derivative is one or more kinds of a quinone molecule selected from the group consisting of 2-(3-carboxypropyl)-3-methyl-1,4-naphthoquinone ($CPVK_3$) represented by the following formula (1), 2-{3-[N-(2-aminoethyl)aminocarbonyl]propyl}-3-methyl-1,4-naphthoquinone ($AEACPVK_3$) represented by the following formula (2), and 2-(3-aminopropyl)-3-methyl-1,4-naphthoquinone ($APVK_3$) represented by the following formula (3).

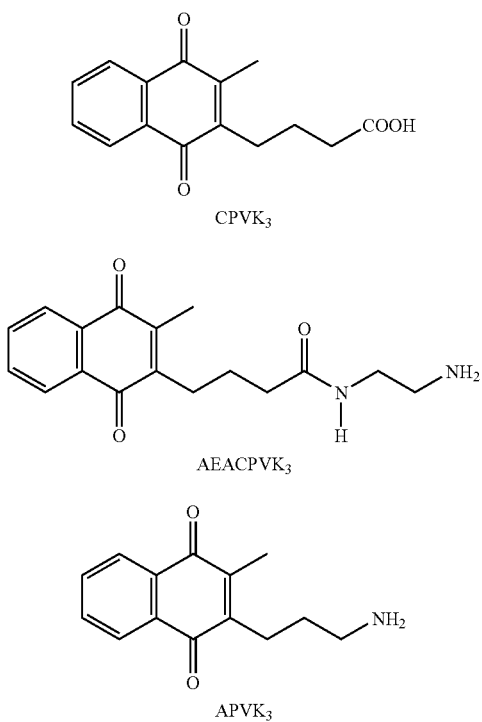

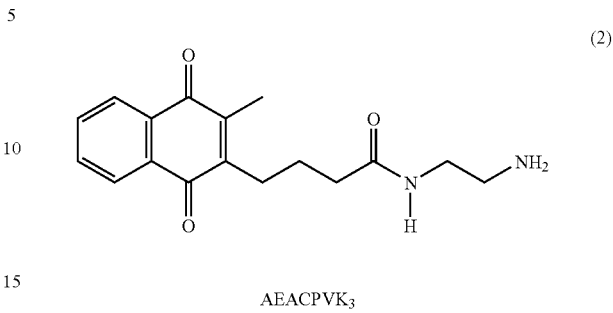

(21) 2-{3-[N-(2-aminoethyl)aminocarbonyl]propyl}-3-methyl-1,4-naphthoquinone (AEACPVK$_3$) represented by the following formula (2).

(7) An electrode including a mediator according to any one of items (1) to (6) immobilized.

(8) An electrode according to item (7), further including an enzyme immobilized.

(9) An electrode according to item (8), in which the enzyme contains diaphorase.

(10) An electrode according to item (8), in which the enzyme contains diaphorase and dehydrogenase.

(11) An electrode according to item (10), in which the dehydrogenase is glucose dehydrogenase.

(12) An electrode according to item (10) or (11), further including NADH immobilized.

(13) An electrode according to any one of items (8) to (12) including the mediator and the enzyme immobilized on the electrode by a polymer and a crosslinking agent.

(14) An electrode according to item (13), in which the polymer is polyvinylimidazole.

(15) An electrode according to item (13) or (14), in which the crosslinking agent is polyethylene glycol diglycidyl ether (PEGDGE).

(16) An electrode according to any one of items (7) to (15), further including an oxygen separation membrane arranged in the vicinity of the mediator.

(17) An electrode according to any one of items (7) to (16), used for a biofuel cell or a biosensor.

(18) A biofuel cell including an enzyme, a substrate (fuel), and electrodes and utilizing electron transfer among the enzyme, the substrate (fuel), and the electrodes for electricity generation, including a cathode and an anode according to any one of items (7) to (17) for the electrodes.

(19) A biofuel cell according to item (18), in which the substrate (fuel) is glucose.

(20) A biofuel cell according to item (18) or (19), in which the cathode contains polydimethylsiloxane immobilized.

According to the present invention, a sufficient amount of the mediator can be easily and strongly immobilized on the electrode that conducts electron transfer between an enzyme and an electrode without impairing functionality as a mediator using a quinone molecule derivative as a mediator. Therefore, an electrode having a high fuel utilization rate can be obtained, and a highly efficient, miniature biofuel cell can be obtained using the electrode. Further, the electrode is highly safe and can be used for an implanted biological device.

DESCRIPTION OF THE INVENTION

Electron transfer in electrolytic oxidation of a substrate (fuel) using a mediator will be described according to FIG. 1 with glucose as a substrate (fuel), for example.

Figure 1:
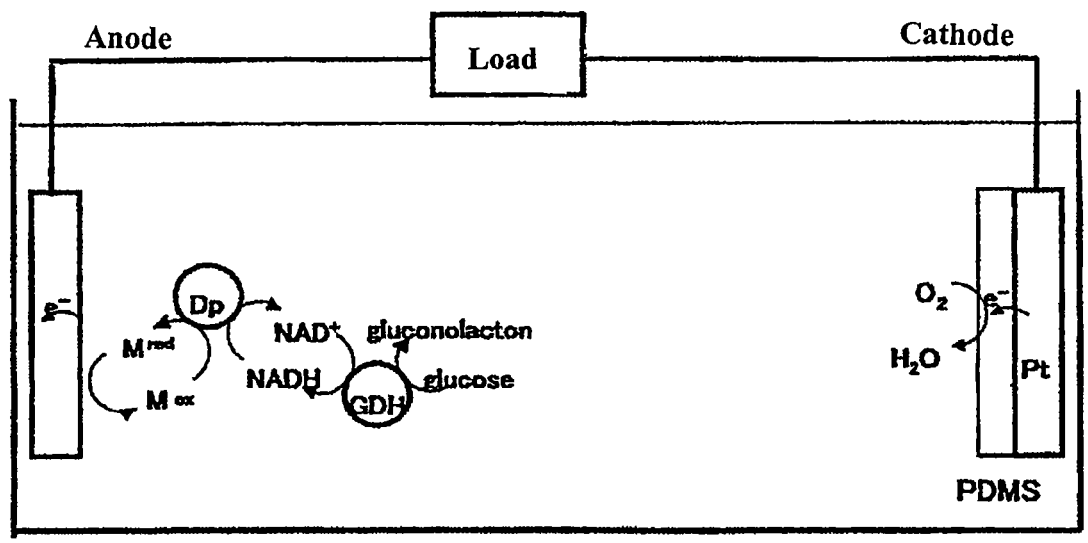
FIG. 1 is a schematic diagram showing a reaction of a cell of the present invention.

FIG. 1 shows a biofuel cell. An oxidation reaction of glucose proceeds at an anode, and a reduction reaction of oxygen proceeds at a cathode. An enzyme required for glucose oxidation (glucose dehydrogenase (GDH), in this case), a coenzyme (NADH), diaphorase (Dp), and a mediator (VK$_3$ derivative) act at the anode to take electrons discharged from the oxidation reaction of glucose out of a system.

Figure 2:
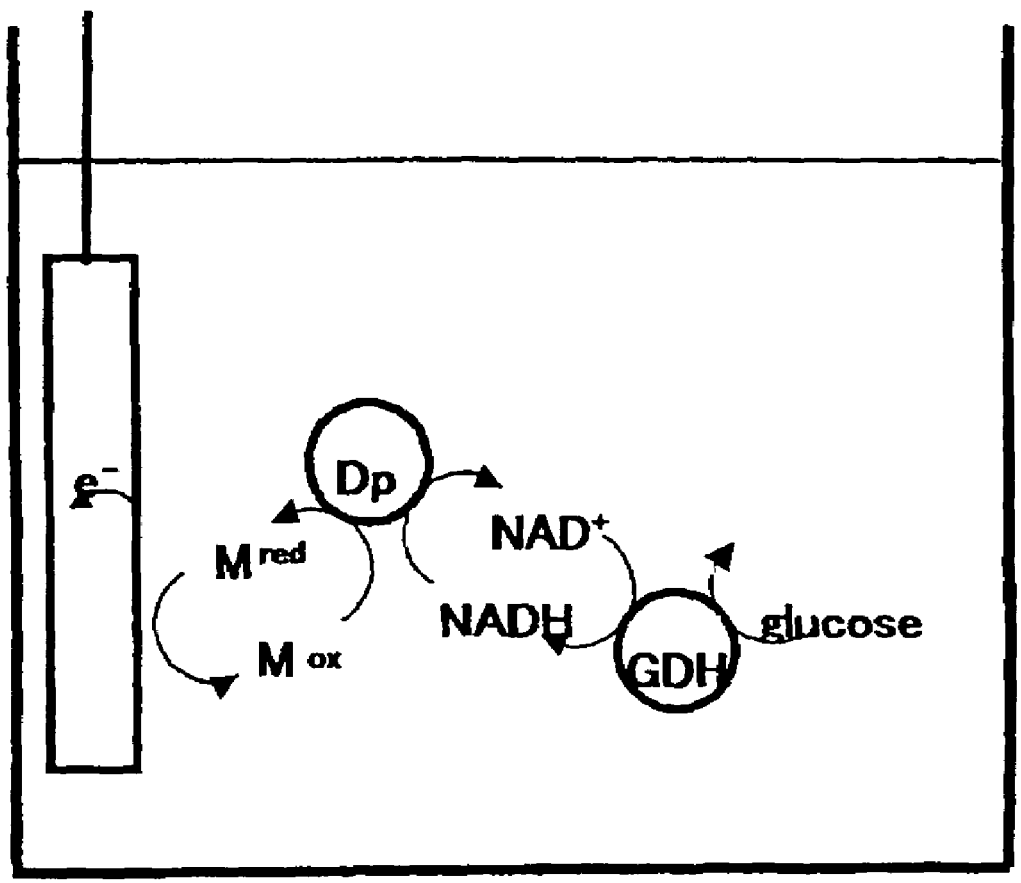
FIG. 2 is a schematic diagram showing a reaction of a sensor of the present invention.

Here, a biofuel cell involves taking the electrons out of a system, and a glucose sensor which measures glucose concentration involves measuring the electrons (FIG. 2).

The glucose is used as a fuel or a measuring object here. However, the fuel or the measuring object can be changed to a different substance, and various dehydrogenase enzymes reacting with the different substance can be used. Examples of such a combination of a fuel or a measuring object and a dehydrogenase enzyme that can be used include lactic acid and lactate dehydrogenase, and alcohol and alcohol dehydrogenase.

Further, mixing or collectively using two or more kinds of the combination allows dealing with variety of fuels for cells.

According to the specifications of the present invention, words "quinone molecule" and "naphthoquinone molecule" refer to "molecule having quinone skeleton" and "molecule having naphthoquinone molecule", respectively. Examples of the "naphthoquinone molecule" include naphthoquinone and anthraquinone.

Quinone molecule derivatives are used for a mediator, and of those, a naphthoquinone molecule derivative is preferable. Further, a mediator composed of a sodium anthraquinone-2-sulfonate (AQS) derivative or a 2-methyl-1,4-naphthoquinone ($VK_3$) derivative is more preferable, and a mediator composed of a $VK_3$ derivative is most preferable.

The derivative, for its purpose, must have a quinone skeleton, and in addition, must be modified with a functional group capable of bonding with a polymer or an enzyme.

The derivative must be modified with a functional group capable of bonding with a polymer described below or a biopolymer such as an enzyme. The polymer contains two or more functional groups selected from the group consisting of an amino group, a carboxyl group, a formyl group, a hydroxyl group, a halogen group, a dihydro-2,5-furandion-1-yl group, and a glycidyl group. Examples of the polymer include polyvinyl imidazole, polylysine, polyallylamine, polyvinylpyridine, polypyrrole, polyacrylic acid, polyvinyl alcohol, a graft copolymer of polypropylene and maleic anhydride, and an ortho-cresol novolac epoxy resin. The derivative is preferably modified with a functional group selected from the group consisting of an amino group, a carboxyl group, a chloroformyl group, a succinimide oxycarbonyl group, an alkyl metal sulfosuccinimide oxycarbonyl group, a pentafluorophenyl oxycarbonyl group, a p-nitrophenyl oxycarbonyl group, a hydroxyl group, a formyl group, a halogen group, a maleimide group, an isothiocyanate group, and an oxiranyl group.

Further, a spacer molecule can be provided between the functional group and the quinone skeleton at an appropriate distance from both. A length or a component molecule of the spacer molecule can be suitably changed depending on a kind of the polymer or the enzyme to which the mediator molecule bonds without impairing functions as a mediator. Examples of the spacer molecule include a hydrocarbon linear chain, a polyoxyethylene linear chain, a polyethylene glycol chain, and a polypropylene glycol chain. The spacer molecule may contain an amide group or the like within the chain. The spacer molecule preferably has a length within the range of 3 to 50 carbon atoms when the carbon atoms are aligned.

The whole mediator molecule can be provided with appropriate hydrophilicity and hydrophobicity from such modification with a functional group or such a spacer molecule, and the functions of the mediator may be further easily exhibited.

Specific examples of the quinone molecule derivative as a mediator include sodium aminoanthraquinone-2-sulfonate (AAQS), 2-(3-carboxypropyl)-3-methyl-1,4-naphthoquinone ($CPVK_3$), 2-{3-[N-(2-aminoethyl)aminocarbonyl]propyl}-3-methyl-1,4-naphthoquinone ($AEACPVK_3$), and 2-(3-aminopropyl)-3-methyl-1,4-naphthoquinone ($APVK_3$).

Two or more kinds of the mediator can be used in combination without impairing an effect of the present invention.

The mediator molecule was evaluated by cyclic voltammetry (CV) through studies of redox potentials and enzyme reaction kinetic analysis.

[Cyclic Voltammetry (CV), Redox Potential of Mediator Molecule]

CV is a method of recording a current while changing a potential of an electrode at a constant rate and shows at which potential and to what extent a reaction takes places. The obtained voltammogram represents the potential on an abscissa axis and the current on an ordinate axis. The CV involves relatively easy experiments and sharply reflects not only equilibrium parameters such as the redox potential or diffusion information but also kinetic parameters of an electrode reaction or of a chemical reaction in solution. Thus, the CV is a method of electrochemical measurement allowing an intuitive grasp of the electrode reaction.

[Reaction Kinetic Analysis of Mediator Molecule]

A technique of reaction kinetic analysis between an enzyme and a mediator molecule using CV will be described referring to a document (Kazuyoshi Takagi, Kenji Kano, Tokuji Ikeda, J. Electroanal. Chem., 1988, 445, 211-219). Dp catalyses an oxidation reaction of NADH in the presence of an appropriate mediator ($M_{ox}$) as represented by the following equation (4).

$$NADH + M_{OX} \underset{v_{E,red}}{\overset{v_{E,ox}}{\rightleftharpoons}} NAD^+ + M_{red} \qquad (4)$$

$M_{ox}$: oxidized mediator $M_{red}$: reduced mediator

An NADH oxidation rate ($v_{E, ox}$) may be represented by the following equation (5) on an assumption that an enzyme reaction follows a ping-pong mechanism.

$$v_{E,ox} = \frac{k_{cat,ox}[Dp]}{1 + \frac{K_{NA,ox}}{[NADH]} + \frac{K_{M,ox}}{[M_{ox}]}} \qquad (5)$$

$k_{cat, ox}$: catalyst constant $K_{NA, ox}$: Michaelis constant of NADH $K_{M, ox}$: Michaelis constant of $M_{ox}$ $M_{red}$ is electrochemically re-oxidized to $M_{ox}$ at a respectively suitable electrode potential with a bioelectrocatalyst employing a mediator molecule. As described, $M_{ox}$ acts as an oxidized mediator molecule on electron transfer from reduced Dp ($Dp_{red}$) to the electrode.

The enzyme reaction exhibits steady properties with large NADH concentration polarization, when NADH concentration is very large compared to negligibly small $K_{NA, ox}$ ([NADH]>>$K_{NA, ox}$) in a vicinity of an electrode surface. In addition, $v_{E, ox}$ of equation (5) can be approximated as the following equation (6) when $M_{ox}$ concentration is negligibly small ([$M_{ox}$]<<$K_{M, ox}$) in the vicinity of the electrode surface.

$$v_{E,ox} = \frac{k_{cat,ox}[Dp][M_{ox}]}{K_{M,ox}} \qquad (6)$$

From the above, $k_{cat, ox}/K_{M, ox}$ clearly represents a reaction rate constant between $DP_{red}$ and $M_{ox}$. Further, steady state limiting current of catalyst ($I_{s, ox}$) observed at a more positive potential from the redox potential of the mediator molecule can be represented by the following equation (7).

$$I_{s,ox} = nFA[M]\sqrt{\frac{D_M k_{cat,ox}[Dp]}{K_{M,ox}}} \quad (7)$$

F: Faraday constant
A: electrode surface area
$D_M$: diffusion coefficient of mediator molecule
n: number of reacting electrons of mediator molecule The reaction rate constant $k_{cat,\ ox}/K_{M,\ ox}$ can be estimated from the measured limiting current value using the above equation (7).

Figure 3:
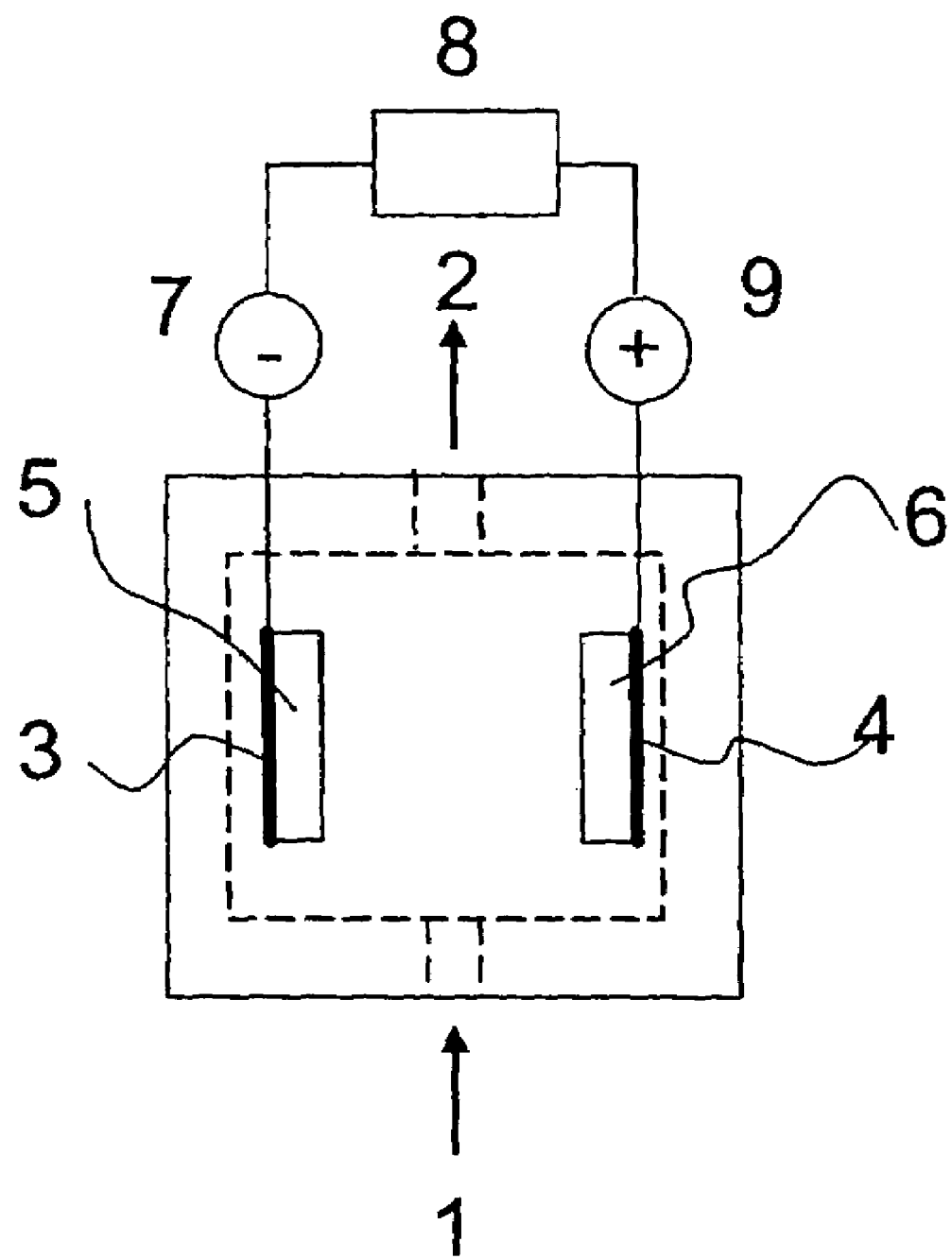
FIG. 3 shows a schematic diagram of a cell of the present invention.

Hereinafter, reactions at respective electrodes using glucose as a substrate (fuel) will be described based on FIG. 3.

A fuel solution is introduced inside a tank boxed with a broken line from a fuel solution inlet 1. An anode 3 and a cathode 4 are arranged inside the tank. The anode has a mediator and, as required, various enzymes immobilized on an anode surface. Further, the cathode may be covered with an oxygen permeable membrane 6 for protection as in FIG. 3. Electrons are taken out from the fuel through a mediator immobilized on the anode and drawn out from the anode to a negative terminal 7. The electrons are passed through an external load 8 and are transmitted from a positive terminal 9 to the cathode 4.

An anode reaction involves a redox cycle of glucose, glucose oxidoreductase (glucose oxidoreductase, glucose dehydrogenase), a coenzyme, diaphorase, and the anode through a mediator. The anode surface is provided with the mediator immobilized thereon. Immobilization of the mediator prevents diffusion of the mediator in the solution. Thus, short circuit of a cell caused by a damage of a separator between the anode and the cathode does not need to be taken into consideration, allowing application of the mediator for a separator-free biofuel cell for miniaturization or simplification.

An enzyme preferably contains both an enzyme containing NADH as a substrate and catalyzing the electron transfer between the oxidized mediator ($M_{ox}$) and the anode, and a dehydrogenase containing $NAD^+$ as a coenzyme. Examples of the former enzyme include diaphorase and ferredoxin-$NADP^+$ reductase (FNR). Of those, diaphorase is most preferable.

The former enzyme is desirably immobilized on the anode surface as well

Examples of the latter enzyme include various dehydrogenases, but GDH is desirable when glucose is used as a substrate (fuel).

Further, the latter enzyme is desirably immobilized on the anode surface as well.

Further, the mediator and the enzyme are more desirably immobilized on the electrode by a polymer or a crosslinking agent.

Examples of the polymer include polyvinyl imidazole (PVI), polyallylamine, polyamino acid (polylysine, for example), polypyrrole, polyacrylic acid, polyvinyl alcohol, a graft copolymer of polypropylene and maleic anhydride, a copolymer of methyl vinyl ether and maleic anhydride, and an ortho-cresol novolac epoxy resin. Further, examples of the crosslinking agent include polyethylene glycol diglycidyl ether (PEGDGE), glutaraldehyde, disuccinimidyl suberate, and succinimidyl-4-(p-maleimidephenyl)butyrate. In addition, the crosslinking agent can be selected referring to a section of crosslinking agents (available from Pierce Biotechnology, Inc.) in a 2001-2002 catalog of Perbio Science UK Ltd. or the like.

A reaction mechanism for immobilizing the $VK_3$ derivative modified with an amino group as a mediator using PVI as a polymer and PEGDGE as a crosslinking agent is as follows. An imidazole group of the PVI bonds with an epoxy group of the PEGDGE, and the other epoxy group of the PEGDGE bonds with amino groups of a mediator molecule and an enzyme to increase a molecular weight and to form an insoluble gel. The insoluble gel is immobilized on an electrode.

The quinone molecule has a problem in that it is easily auto-oxidized, and dissolved oxygen in the fuel solution acting on the anode causes a decrease of a voltage. Therefore, a means for consuming oxygen may be provided to prevent the oxygen from reaching the anode surface. An enzyme for consuming oxygen may be dissolved in the fuel solution, for example.

Examples of the enzyme for consuming oxygen include so-called oxidases. Glucose oxidase (GOD) oxidizes glucose, which is a fuel, while reducing and consuming oxygen. The oxygen concentration in the solution is decreased by actions of those oxidases, allowing prevention of an increase of an anode potential, that is, a decrease of a cell voltage.

However, the enzyme is a cathode reactant and desirably exists in high concentration at a cathode surface. Therefore, an enzyme consumption reaction by the oxidase desirably proceeds only in the vicinity of the anode, and the oxidase may be effectively arranged at the anode surface or in the vicinity of the anode, for example. Examples of methods for arranging the oxidase at the anode surface or in the vicinity of the anode include: immobilizing the enzyme on a carrier; and arranging an oxygen separation membrane with the enzyme added at the surface or in the vicinity of the anode instead of simply dissolving the enzyme for consuming oxygen.

Further, an enzyme other than GOD, which uses glucose for consumption of oxygen, such as ascorbic acid oxidase is desirably employed when using an oxidase for a glucose sensor because a measurement object is glucose.

Figure 4:
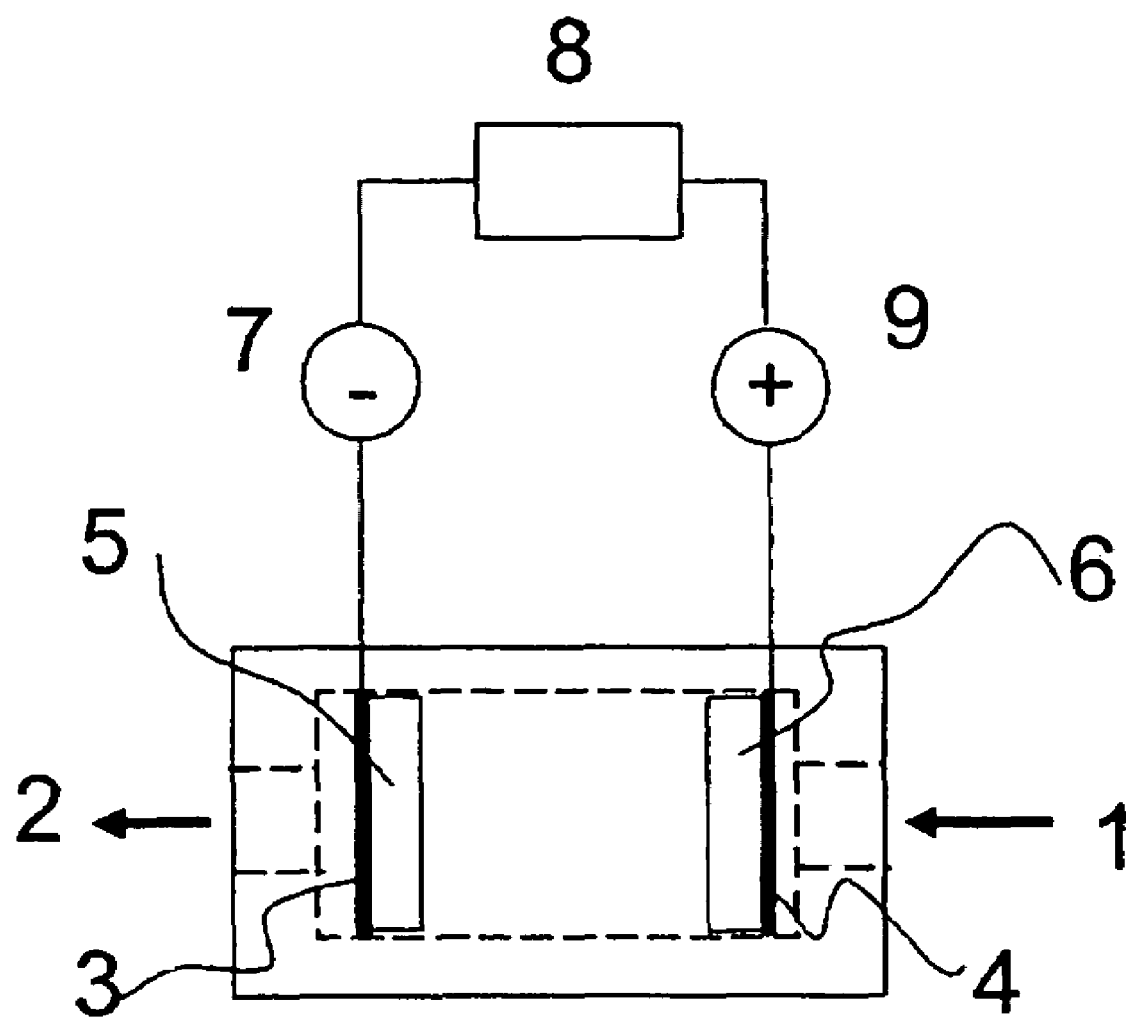
FIG. 4 shows a schematic diagram of a cell of the present invention (arranging inlet close to cathode)

In addition, a cell structure as in FIG. 4 allows removal of the oxygen in the fuel solution. In other words, a fuel solution is introduced into a system from a fuel solution inlet 1. The fuel solution first comes in contact with a cathode 4. The cathode 4 in a form of a mesh or a porous plate allowing liquid passage consumes oxygen while the oxygen passes through the cathode 4. Such a structure can remove the oxygen, which adversely affects the mediator, without particularly arranging the oxygen separation membrane.

Examples of the cathode that can be used include: an electrode of a precious metal such as platinum which is effective for a reduction reaction of oxygen; and a conductive electrode such as graphite supporting fine particles of platinum or the like with catalytic property.

Further, the cathode surface may also be modified with a membrane exhibiting oxygen selectivity (oxygen separation membrane 6 in FIG. 3) for reducing an effect of the impurities or the like on cathode characteristics. Examples of such a membrane include a membrane composed of polydimethylsiloxane (PDMS) and having porosity and hydrophobicity. The oxygen separation membrane can prevent penetration of electrochemically interfering substances to the electrode and maintain electrode performance.

A neutral aqueous solution is used for an electrolytic solution. A neutral aqueous buffer solution capable of reducing a pH change is preferable, and examples thereof include a phosphate buffer solution and a Tris buffer solution.

The CV for mediator evaluation involves measuring in an electrolytic solution consisting of the buffer with various mediators, diaphorase, and NADH added.

Further, the CV for electrode (anode) evaluation involved using an electrode with various mediators and various enzymes immobilized and using the buffer consisting of NADH and glucose as a fuel added.

[Anode Evaluation—chronopotentiometry—]

Chronopotentiometry is a method for evaluating characteristics of a cell electrode involving: measuring an electrode potential of a working electrode while conducting constant current electrolysis; and obtaining a relationship between potential and time.

The cathode of the cell according to the present application can be widely used without particular limitation. Thus, evaluation centered on mainly the anode by chronopotentiometry and CV represents cell evaluation.

AAQS, $VK_3$, $AEACPVK_3$, and $APVK_3$ of the quinone derivatives according to the present invention were synthesized as follows.

[AAQS Synthesis]

AAQS is synthesized through the following equations (8) and (9).

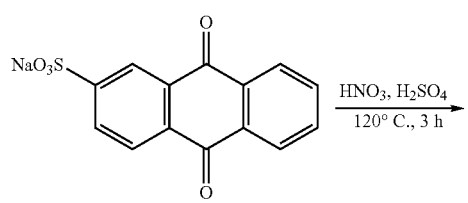

(8)

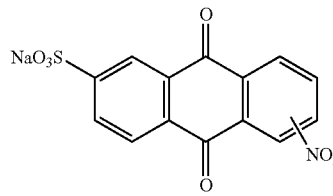

Sodium anthraquinone-2-sulfonate was dissolved in concentrated sulfuric acid, and the mixture was heated and stirred at 50° C. Fuming nitric acid was added to the mixture, and the mixture was heated to 120° C. and stirred for 3 hours, retaining the temperature. Temperature of the reaction mixture was returned to room temperature, and the reaction mixture was poured into an ice bath for cooling. Then, a 50% aqueous solution of sodium hydroxide was added so that the mixture became alkaline (pH of 10 or more), and a precipitated solid was collected by filtration. The solid was sufficiently washed with a cooled 2% aqueous solution of sodium sulfate and dried under reduced pressure, to obtain a pinkish brown solid. The solid was probably nitrated sodium anthraquinone-2-sulfonate for the following reasons and was used for the next reduction step. The reasons include that: sodium anthraquionone-2-sulfonate, which is a raw material, was not detected by TLC of the solid; signals specific to sodium anthraquionone-2-sulfonate was not detected by $^1$H-NMR of the solid; and the solid had much higher water-solubility than the sodium anthraquionone-2-sulfonate.

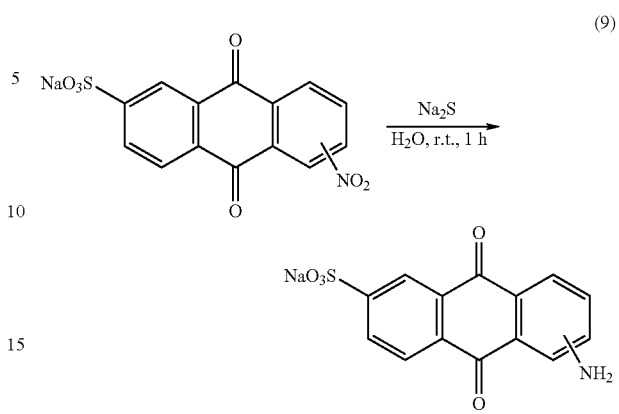

The nitrated sodium anthraquionone-2-sulfonate was dissolved in water. Sodium sulfide nonahydrate was added to the mixture, and the mixture was stirred at room temperature for 1 hour. The reaction mixture turned deep red with progress of the reaction. The reaction mixture was saturated with sodium chloride and extracted with 2-propanol. A 2-propanol layer was concentrated under reduced pressure, diluted with water, and subjected to preparative HPLC, to thereby obtain 2 kinds of red powders of sodium amino anthraquionone-2-sulfonate (AAQS1, AAQS2).

$^1$H-NMR ($D_2O$) of AAQS1: 8.08-8.00 (m, 1H), 7.95-7.88 (m, 1H), 7.86-7.78 (m, 1H), 6.98-6.8 (m, 2H), and 6.56-6.47 (m, 1H)

$^1$H-NMR ($D_2O$) of AAQS2: 8.09-7.99 (m, 1H), 7.88-7.75 (m, 2H), 6.97-6.85 (m, 2H), and 6.54-6.46 (m, 1H).

[$CPVK_3$ Synthesis]

$CPVK_3$ is synthesized through the above equation (10).

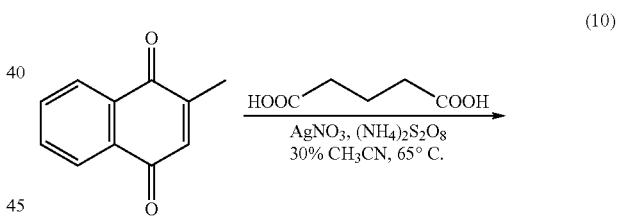

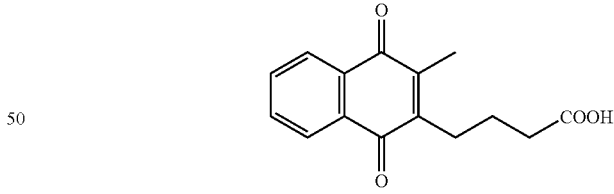

The $CPVK_3$ was synthesized referring to a document (Salmon-Chemin L., Buisine E., Yardley V., Kohler S., Debreu M. A., Landry V., Sergheraert C., Croft S. L., Krauth-Siegel R. L., and Daviould-Charvet E., J. Med. Chem., 2001, 44, 548-565). 2-methyl-1,4-naphthoquinone, glutaric acid, and $AgNO_3$ were suspended in a 30% aqueous $CH_3CN$ solution, heated, and stirred to dissolve completely. Then, a 30% aqueous $CH_3CN$ solution of $(NH_4)_2S_2O_8$ was added dropwise in 60 minutes. After completing the dropwise addition, the mixture was stirred at 65° C. for 5 minutes as it was. Cooling of the reaction mixture to room temperature resulted in precipitation of a yellow brown solid. Water and ethyl acetate were added to the reaction mixture, and an organic layer was washed with water using a separating funnel. Further, the organic layer was washed with water. A 2N-aqueous solution of sodium bicarbonate was added to the organic layer, and a sodium salt of a target compound was extracted to an aqueous layer. Then, the aqueous layer was adjusted to a pH of 2 or less using 37% hydrochloric acid, and a precipitated solid was collected by filtration. The solid was sufficiently washed with cool water, and dried under reduced pressure, to thereby obtain a yellow brown powder 2-(3-carboxypropyl)-3-methyl-1,4-naphthoquinone.

[AEACPVK$_3$ Synthesis]

AEACPVK$_3$ is synthesized through the above equation (11).

(11)

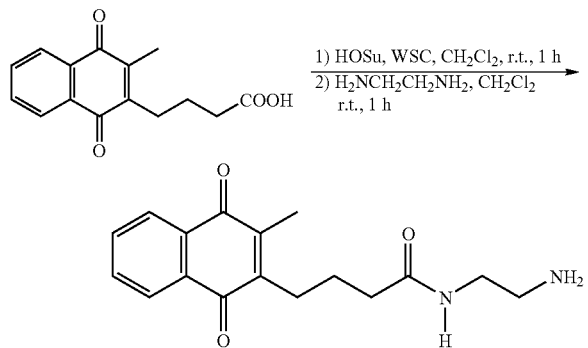

2-(3-carboxypropyl)-3-methyl-1,4-naphthoquinone (1.00 g, 3.9 mmol) and N-hydroxysuccinimide (534 mg, 4.64 mmol) were dissolved in dichloroethane (80 ml). WSC (EDC) (890 mg, 4.64 mmol) was added to the mixture, and the mixture was stirred for 4 hours. 2.59 ml of ethylenediamine (2.33 g, 38.7 mmol) was dissolved in dichloromethane (10 ml), and the above reaction mixture was added thereto dropwise in 15 minutes. The mixture was stirred as it was at room temperature for 2 nights. Dichloromethane (300 ml) was added to the reaction mixture, and the reaction mixture was washed with water (500 ml×1). An organic layer was dried using sodium sulfate. A solvent was removed under reduced pressure, and the mixture was purified using a silica gel chromatography (silica gel: Fuji Silysia NH-DM1020; dichloromethane:methanol=96:4) and recrystallized (dichloromethane:hexane), to thereby obtain a yellow brown powder of 2-{3-[N-(2-aminoethyl)aminocarbonyl]propyl}-3-methyl-1,4-naphthoquinone (yield: 686 mg, 2.29 mmol, 58.9%).

$^1$H-NMR (CDCl$_3$): 8.09-8.05 (m, 2H), 7.73-7.65 (m, 2H), 6.33 (br, 1H), 3.37 (q, J=5.6 Hz, 2H), 2.90 (t, J=5.6 Hz, 2H), 2.68 (t, J=8.0 Hz, 2H), 2.32 (t, J=7.2 Hz, 2H, 222 (s, 3H), and 1.83 (m, 2H).

[APVK$_3$ Synthesis]

APVK$_3$ is synthesized through the above equations (12) and (13).

(12)

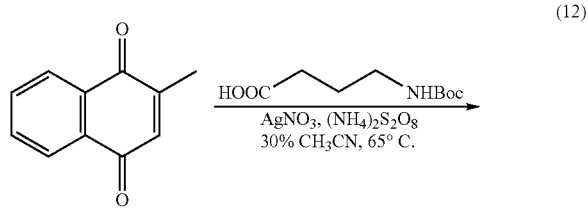

-continued (13)

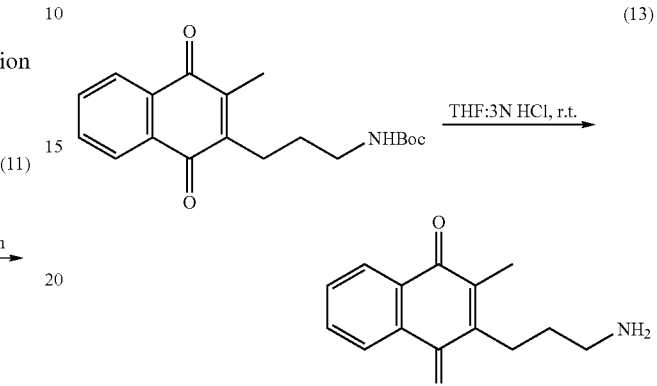

2-methyl-1,4-naphthoquinone, N-tert-BOC-γ-butyric acid, and AgNO$_3$ were suspended in a 30% aqueous CH$_3$CN solution, heated, and stirred at 65° C. to dissolve completely. Then, a 30% aqueous CH$_3$CN solution of (NH$_4$)$_2$S$_2$O$_8$ was added dropwise in 2 hours while heating and stirring the mixture at 65° C. After completing the dropwise addition, the mixture was stirred for 10 minutes as it was. The temperature of the reaction mixture was returned to room temperature. Ethyl acetate was added to the reaction mixture, and an organic layer was washed with water. Then, the organic layer was washed with a 5% aqueous solution of sodium bicarbonate and saturated saline solution, and was dried using sodium sulfate. A solvent was removed under reduced pressure, and the mixture was purified using a silica gel chromatography, to thereby obtain yellow brown oil of 2-[3-(N-tert-BOC-γ-amino)propyl]-3-methyl-1,4-naphthoquinone. The oil was dissolved in a mixed solvent of THF and 37% hydrochloric acid, and the mixture was mixed at room temperature overnight. The THF was removed under reduced pressure, and water was added. An aqueous layer was washed with dichloromethane. Sodium bicarbonate was added to the aqueous layer to adjust the reaction mixture to alkaline. A target compound was extracted to an organic layer by ethyl acetate, and the organic layer was dried using sodium sulfate. The solvent was distilled off under pressure, to obtain a dark brown powder of 2-(3-aminopropyl)-3-methyl-1,4-naphthoquinone.

EXAMPLE 1

Various mediators were evaluated through CV and reaction rate kinetic analysis.

(1) Cyclic Voltammetry (CV)

A potentiostat mode of Hokuto Denko HZ-3000 was used. A glassy carbon electrode (GDE, electrode area of about 0.083 cm$^2$) was used as a working electrode. The GDE was polished with an aluminum powder of 0.05 μm and subjected to ultrasonic cleaning in deionized water before every measurement. A three electrode cell was used, and a Pt electrode and an Ag|AgCl (saturated KCl) electrode were used as a counter electrode and a reference electrode, respectively for the measurement. A potential was changed at a rate of 5 mV/s. A measurement sample was subjected to sufficient bubbling with $N_2$ gas before the measurement to remove dissolved oxygen, and the $N_2$ gas overflowed during the measurement. All measurements began from an open circuit potential.

Figure 5:
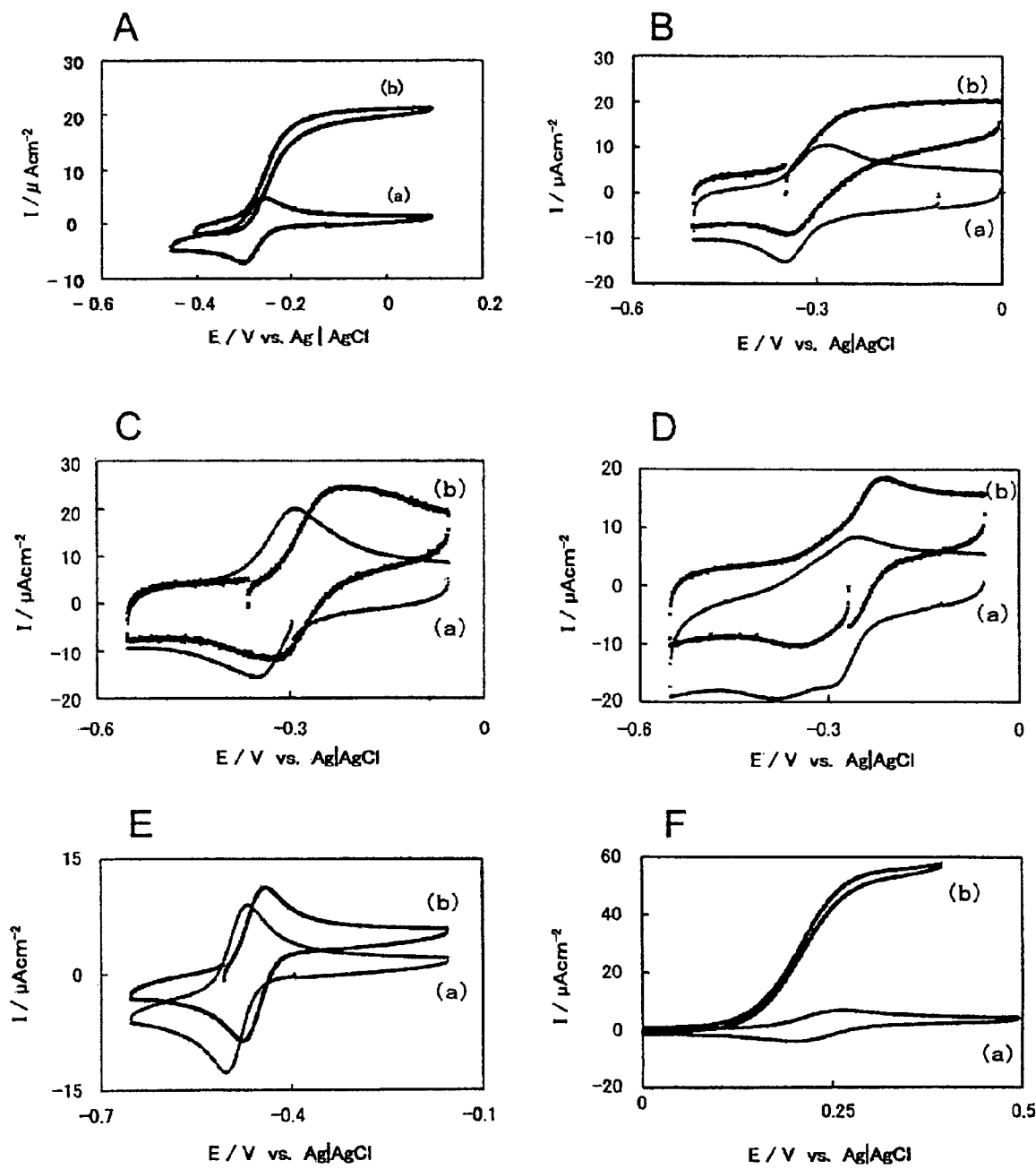
FIG. 5 shows cyclic voltammograms of respective mediators.

FIG. 5 shows cyclic voltammograms of various mediators. FIG. 5 shows the results of $VK_3$ (FIG. 5A), $CPVK_3$ (FIG. 5B), $AEACPVK_3$ (FIG. 5C), $APVK_3$ (FIG. 5D), anthraquinone sulfonic acid (AQS, FIG. 5E), and ferrocene methanol (FMA, FIG. 5F).

Cyclic voltammograms with (a) in FIGS. 5A to 5F are measurement of 0.09 mM solutions of the various mediators prepared using a Tris buffer solution (pH 8.5). All the cyclic voltammograms include clear current peak pairs corresponding to reduction reactions and oxidation reactions. The results show that all the molecules exemplified here can carry out reversible electrode reactions. Further, redox formal potentials ($E^0_M{}'$) approximated at middle points of oxidation peaks and reduction peaks are −0.28 V ($VK_3$), −0.32 V ($CPVK_3$), −0.32 V ($AEACPVK_3$), −0.32 V ($APVK_3$), −0.49 V (AQS), and 0.23 V (FMA).

On the other hand, cyclic voltammograms with (b) in FIGS. 5A to 5F are measurement results of the above mediator solutions with 0.11 μM of Dp (DIAPHORASE I, [EC 1.6.99.-], from *Bacillus stearothermophilus*, available from Unitika Ltd.) and 4.8 mM of NADH added. Oxidation current increased because the mediators oxidized at the electrode were reduced by Dp and NADH to take part in an electrode reaction again. The increased oxidation current confirms that electron transfer from NADH to the mediators proceeded through Dp. In other words, all the molecules exemplified here may impart or receive electrons to or from an active center of Dp (FAD) and may function as mediators.

Similar results were obtained when the mediators were immobilized on electrodes.

(2) Reaction Kinetic Analysis

Figure 6:
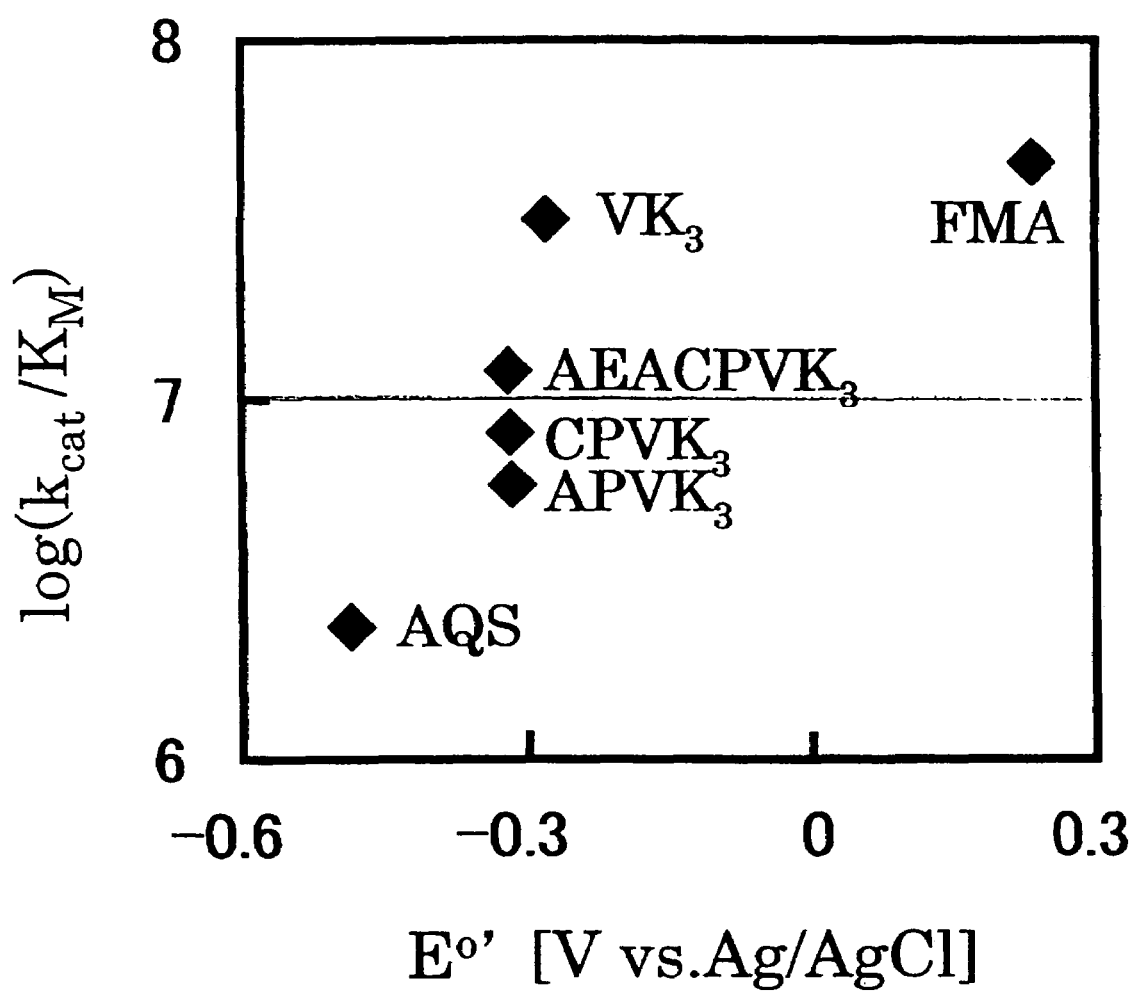
FIG. 6 shows a logarithmic plot of rate constants versus $E^{0}{}_{M}{}'$ of respective mediators.

Reaction rate constants between $Dp_{red}$ and $M_{ox}$ were estimated from the equation (7) using values of steady state limiting current of catalyst ($I_{s, ox}$) obtained from FIGS. 5A to 5F. The number of electrons in reaction (n) was two for a quinone molecule and one for FMA. A diffusion coefficient ($D_M$) of hydroquinone was used. FIG. 6 can be obtained by logarithmically plotting the obtained reaction rate constants ($k_{cat, ox}/K_{M, ox}$) with respective $E^0_M{}'$ of the mediator molecules.

First, a comparison on characteristics of the mediators focusing on FMA, $VK_3$, and AQS concluded that the FMA was kinetically most advantageous, with a reaction rate constant larger than that of the AQS by 1 digit or more. The rate constant of the $VK_3$ fell short of that of the FMA, but was a comparably large value. On the other hand, the redox potential $E^0_M{}'$ is also an important value representing physical property, and a difference with a cathode potential primarily defines the cell voltage. For example, the FMA, which had an $E^0_M{}'$ close to a cathode reaction ($O_2$ reduction) potential (about 0.3 V), is not suitable for an anode mediator. Conditions of a mediator for a high-output cell include "large reaction rate constant and more negative $E^0_M{}'$", and $VK_3$ was confirmed to be advantageous in this regard.

The $VK_3$ derivatives of $AEACPVK_3$, $CPVK_3$, and $APVK_3$ had about the same $E^0_M{}'$ as that of the $VK_3$. Further, kinetically, $\log(k_{cat, ox}/K_{M, ox})$ was about 7.0, which was a smaller value than 7.5 of the $VK_3$. However, the derivatives were sufficiently advantageous to the AQS, and the results confirmed that those $VK_3$ derivatives possess conditions as a mediator.

EXAMPLE 2

An enzyme and a mediator ($AEACPVK_3$) were immobilized on the anode, and the anode was evaluated by CV and chronopotentiometry.

(1) Immobilization of Enzyme and Mediator on Anode $AEACPVK_3$, Dp, and GDH, along with a polymer, were immobilized on an electrode using PEGDGE as a crosslinking agent. 7.5 μl of a buffer solution containing 27 units of the Dp (DIAPHORASE I, [EC 1.6.99.-], from *Bacillus stearothermophilus*, available from Unitika Ltd.), 13 μg of the $AEACPVK_3$, 20 units of the GDH, 75 μg of the PVI, and 595 μg of the PEGDGE were applied onto a glassy carbon electrode having a diameter of 3 mm and cured through a 50-h reaction in a desiccator at 4° C. An immobilized electrode was formed by washing with deionized water slowly and carefully after curing.

(2) CV

A potentiostat mode of Hokuto Denko HZ-3000 was used. The electrode with the enzyme and the mediator immobilized prepared in (1) was used as a working electrode. A three electrode cell was used, and a Pt plate and an Ag|AgCl (saturated KCl) electrode were used as a counter electrode and a reference electrode, respectively for the measurement. A potential was changed at a rate of 5 mV/s. A measurement sample was subjected to sufficient bubbling with $N_2$ gas before the measurement to remove dissolved $O_2$, and the $N_2$ gas overflowed during the measurement. All measurements began from an open circuit potential. The measurement was conducted in a Tris buffer solution (pH 8.5). NADH was added to concentration of 0.5 mM, and glucose was added to concentration of 2.0 mM.

Figure 7:
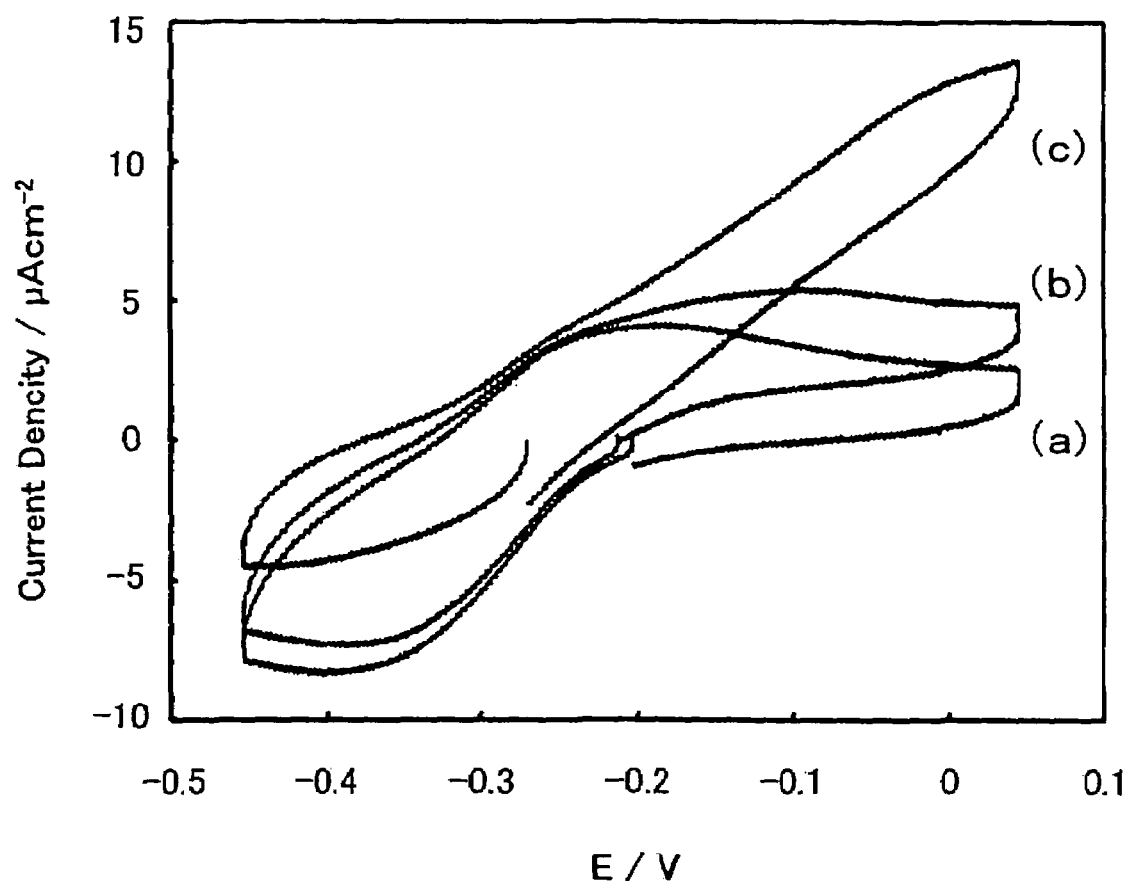
FIG. 7 shows cyclic voltammograms of enzyme-modified electrodes.

FIG. 7 shows cyclic voltammograms of such measurements. The CV with (a) in FIG. 7 was obtained by measuring in a state without the NADH and the glucose, showing redox behavior of the immobilized mediator. The CV shows that a redox reaction occurs in a state with the mediator immobilized along with an enzyme at a similar potential to that in a liberated state (FIG. 5C(a)).

The CV with (b) in FIG. 7 was obtained in a measurement solution with the NADH added. The oxidation current increased, showing that mediation function appears in a state of both the $AEACPVK_3$ and the Dp immobilized.

The CV with (c) in FIG. 7 was CV obtained by measuring in a state with the glucose added. The oxidation current increased greatly, showing that the glucose was oxidized through electrolysis (indirectly). In other words, the results support that the anode reaction shown in FIG. 1 actually proceeded.

(3) Chronopotentiometry

Figure 8:
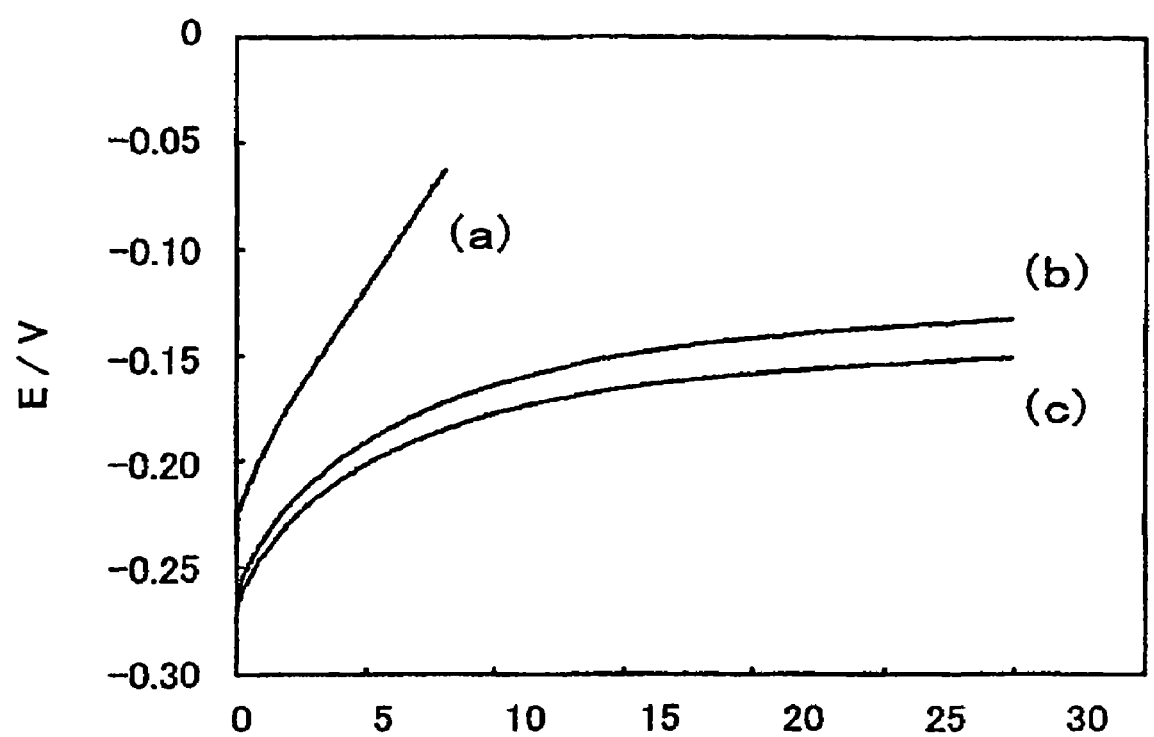
FIG. 8 shows polarization behavior of enzyme-modified electrodes during passing of a constant current.

Chronopotentiometry was conducted by forcibly passing a constant oxidation current (5 μA/cm²) in the same electrolyte solution using the same electrodes as in the CV. FIG. 8 shows the obtained polarization behaviors. (a), (b), and (c) in FIG. 8 represent the same notations as in the CV. The results show that addition of the NADH (b) and addition of the glucose (c) cause the redox potential to remain about −0.15 V vs. Ag|AgCl and that the required oxidation reaction amount (5 μA/cm² equivalent) may be continued at this potential. A power density of a biofuel cell constituted by combining the above components can be estimated to be 2.25 μW/cm² (5

μA/cm²×0.45 V), when a cathode potential by the reduction reaction of $O_2$ is 0.3 V vs. Ag|AgCl, for example.

According to the present invention, sufficient amount of the mediator can be easily strongly immobilized on the electrode without impairing functionality as a mediator, to thereby provide an electrode with a high fuel utilization rate. Therefore, the electrode can be applied to a highly efficient, miniature biofuel cell and can be used for an implanted biological device.

The invention claimed is:

1. An electrode comprising
a mediator, said mediator comprising a quinone molecule derivative,
a crosslinking agent, and
a polymer or a biopolymer,
wherein
the quinone molecule derivative is a quinone molecule modified with at least one functional group bonded with (i) the polymer or the biopolymer or (ii) the crosslinking agent;
the mediator is immobilized through bonding of the at least one modified functional group of the quinone molecule derivative; and
the mediator mediates electron transfer between at least one enzyme and an electrode.

2. An electrode according to claim 1, wherein the at least one enzyme is immobilized.

3. An electrode according to claim 2, wherein the at least one immobilized enzyme is diaphorase.

4. An electrode according to claim 2 comprising at least two immobilized enzymes, wherein the at least two immobilized enzymes are diaphorase and dehydrogenase.

5. An electrode according to claim 4, wherein the dehydrogenase is glucose dehydrogenase.

6. An electrode according to claim 4 or 5, further comprising immobilized co-enzyme NADH.

7. An electrode according to claim 2 comprising the mediator and the enzyme immobilized on the electrode by a polymer and a crosslinking agent.

8. An electrode according to claim 7, wherein the polymer is polyvinylimidazole.

9. An electrode according to claim 7 or 8, wherein the crosslinking agent is polyethylene glycol diglycidyl ether (PEGDGE).

10. An electrode according to claim 1, used for one of a biofuel cell and a biosensor.

11. The electrode according to claim 1 wherein the quinone molecule derivative is a naphthoquinone molecule derivative.

12. The electrode according to claim 11 wherein the naphthoquinone molecule derivative is at least one naphthoquinone molecule chosen from the group consisting of a sodium anthraquinone-2-sulfonate (AQS) derivative and a 2-methyl-1,4-naphthoquionone (VK3) derivative.

13. The electrode according to claim 11, wherein the naphthoquinone molecule derivative is a 2-methyl-1,4-naphthoquinone (VK3) derivative.

14. The electrode according to claim 13, wherein the 2-methyl-1,4-naphthoquinone (VK3) derivative is 2-methyl-1,4-naphthoquinone (VK3) modified with at least one functional group, wherein the at least one functional group is capable of bonding with a polymer or an enzyme.

15. The electrode according to claim 14, wherein the at least one functional group is selected from the group consisting of an amino group, a carboxyl group, a chloroformyl group, a succinimide oxycarbonyl group, an alkyl metal sulfosuccinimide oxycarbonyl group, a pentafluorophenyl oxycarbonyl group, a p-nitrophenyl oxycarbonyl group, a hydroxyl group, a formyl group, a halogen group, a maleimide group, an isothiocyanate group, and an oxiranyl group.

16. The electrode according to claim 15, wherein the 2-methyl-1,4-naphthoquinone (VK3) derivative is modified with the at least one functional group at a 2-position and/or a 3-position of the naphthoquinone.

17. The electrode according to claim 16, wherein the 2-methyl-1,4-naphthoquinone (VK3) derivative is a 3-methyl-1,4-naphthoquinone modified with the at least one functional group at the 2-position of the naphthoquinone.

18. The electrode according to claim 17, further comprised of a spacer molecule between the functional group and the 2-position of the naphthoquinone.

19. The electrode according to claim 18, wherein the spacer molecule is selected from the group consisting of a hydrocarbon linear chain, a polyoxyethylene linear chain, a polyethylene glycol chain, and a polypropylene glycol chain.

20. The electrode according to claim 19, wherein the spacer molecule is a hydrocarbon linear chain alkyl group.

21. The electrode according to claim 14, wherein the 2-methyl-1,4-naphthoquinone (VK3) derivative is one or more kinds of a quinone molecule selected from the group consisting of 2-(3-carboxypropyl)-3-methyl-1,4-naphthoquinone (CPVK3) represented by the following formula (1), 2-{3-[N-(2-aminoethyl)aminocarbonyl]propyl}-3-methyl-1,4-naphthoquinone (AEACPVK3) represented by the following formula (2), and 2-(3-aminopropyl)-3-methyl-1,4-naphthoquinone (APVK3) represented by the following formula (3):

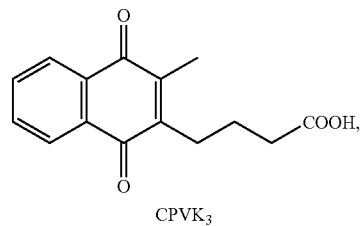

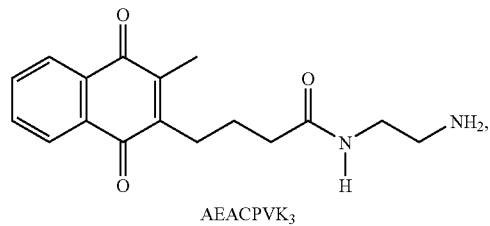

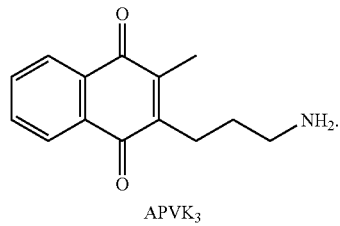

22. The electrode according to claim 21, wherein the 2-methyl-1,4-naphthoquinone (VK3) derivative is 2-(3-carboxypropyl)-3-methyl-1,4-naphthoquinone (CPVK3) represented by the following formula (1):

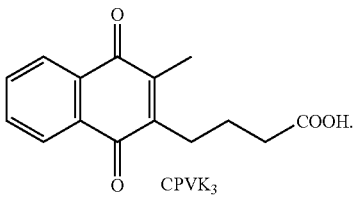

(1)

CPVK₃

23. An electrode according to claim 1 comprising a polymer, wherein
the modified functional group of the quinone molecule derivative of the mediator is bonded to the crosslinking agent; and
the crosslinking agent is bonded to the polymer.

24. An electrode according to claim 23, wherein
the quinone molecule derivative is a quinone molecule modified with an amino functional group;
the polymer comprises an imidazole functional group;
the crosslinking agent comprises at least two epoxy functional group;
the amino functional group of the quinone molecule derivative bonds with a first epoxy functional group of the crosslinking agent;
the imidazole functional group of the polymer bonds with the second epoxy functional group of the crosslinking agent;
the bonded mediator, crosslinking agent, and polymer form an insoluble gel; and
the insoluble gel is immobilized on the electrode.

25. An electrode according to claim 23, wherein the polymer is polyvinylimidazole.

26. An electrode according to claim 23, wherein the crosslinking agent is polyethylene glycol diglycidyl ether (PEGDGE).

27. An electrode apparatus comprising
an electrode with an electrode surface;
a mediator comprising a quinone molecule derivative consisting of 2-(3-carboxypropyl)-3-methyl-1,4-naphthoquinone (CPVK3);
a diaphorase enzyme; and
a nicotinamide adenine dinucleotide molecule;
wherein
the mediator and the diaphorase enzyme are immobilized on the electrode surface by a polyvinylimidazole polymer and a polyethylene glycol diglycidyl ether (PEGDGE) crosslinking agent;
the immobilized diaphorase enzyme can catalyze electron transfer between the immobilized nicotinamide adenine dinucleotide molecule and the immobilized mediator; and
the immobilized mediator mediates electron transfer between the immobilized diaphorase enzyme and the electrode.

28. The electrode of claim 27 further comprising a dehydrogenase enzyme,
wherein
the dehydrogenase enzyme is immobilized on the electrode surface by the polyvinylimidazole polymer and the PEGDGE crosslinking agent;
the immobilized dehydrogenase enzyme can catalyze electron transfer between a biofuel and an oxidized form of the immobilized nicotinamide adenine dinucleotide molecule to form a reduced form of the immobilized nicotinamide adenine dinucleotide molecule; and
the immobilized diaphorase enzyme can catalyze electron transfer between the reduced form of the immobilized nicotinamide adenine dinucleotide molecule and the immobilized mediator.

* * * * *